(12) United States Patent
Buytaert

(10) Patent No.: US 6,359,628 B1
(45) Date of Patent: Mar. 19, 2002

(54) COMBINED IDENTIFICATION AND PREVIEW SYSTEM FOR USE IN DIGITAL RADIOGRAPHY

(75) Inventor: Tom Buytaert, Mortsel (BE)

(73) Assignee: Agfa-Gevaert, Mortsel (BE)

( * ) Notice: Subject to any disclaimer, the term of this patent is extended or adjusted under 35 U.S.C. 154(b) by 0 days.

(21) Appl. No.: 09/168,262

(22) Filed: Oct. 8, 1998

Related U.S. Application Data

(60) Provisional application No. 60/071,641, filed on Jan. 16, 1998.

(30) Foreign Application Priority Data

Oct. 8, 1997 (EP) .............................................. 97203135

(51) Int. Cl.$^7$ .................................................. G09G 5/00
(52) U.S. Cl. ......................... 345/619; 345/629; 250/581
(58) Field of Search ................................ 345/501, 502, 345/507, 1, 1.3, 2, 101, 201, 619, 581, 629; 250/581, 583, 584

(56) References Cited

U.S. PATENT DOCUMENTS

| | | | | |
|---|---|---|---|---|
| 4,960,994 A | * | 10/1990 | Muller et al. | 250/327.2 |
| 5,654,555 A | * | 10/1990 | Buytaert et al. | 250/581 |
| 5,264,684 A | * | 11/1993 | Weil | 235/375 |
| 5,616,930 A | * | 4/1997 | Janssens et al. | 250/584 |

FOREIGN PATENT DOCUMENTS

| | | | | |
|---|---|---|---|---|
| EP | 0 727 696 A1 | * | 2/1995 | G03B/42/04 |
| EP | 0686927 A1 | * | 12/1995 | G06F/19/00 |
| EP | 0727696 A1 | * | 12/1995 | G03B/42/04 |

* cited by examiner

Primary Examiner—Bipin Shalwala
Assistant Examiner—Mansour M. Said
(74) Attorney, Agent, or Firm—John A. Merecki; Hoffman, Warnick & D'Alessandro LLC

(57) ABSTRACT

A combined system for identifying a radiographic image that has been stored in a photostimulable phosphor screen and for displaying a preview image of that image on a single personal computer.

12 Claims, 5 Drawing Sheets

Figure 1:
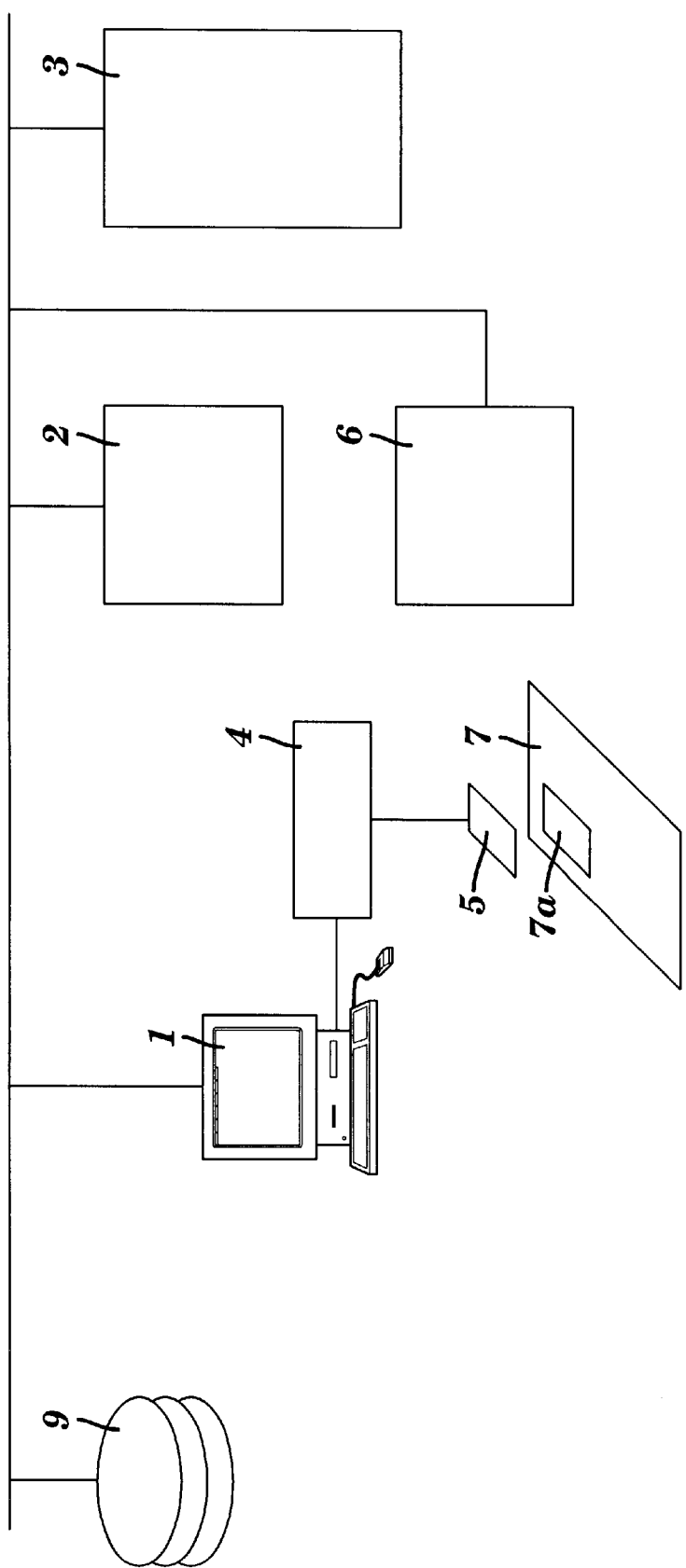

| ADC2 IDENTIFICATION STATION <ADC2/IDEN2> IDENTIFICATION SCREEN | | | | — □ ✕ |
|---|---|---|---|---|
| FILE CONFIGURATION MODE PERFORM HELP | | | | |

PATIENT

| PATIENT NAME | CHARELSAAaaaa 123456 | FIRST NAME | LOUIS 123456789 |
|---|---|---|---|
| BIRTH DATE | 31.08.1945 | PATIENT ID | 450812V019123456 |
| SEX | OTHER ▸ | ACCESSION NUMBER | ris_123456 |

STUDY

| RADIOLOGIST | AGFA DEFAULT M ▸ | | |
|---|---|---|---|
| EXAMINATION | SKULL ▸ | SUB EXAMINATION | GENERAL PA ▸ |

IMAGE

| DEPARTMENT | MC DEPARTMENT ▸ | | |
|---|---|---|---|
| PATIENT POSITION | RL ▸ | EXPOSURE CLASS | 200 ▸ |
| CASSETTE ORIENTATION | PORTRAIT ▸ | | |
| COMMENT | COMMENT AAaaaa | | |

DESTINATIONS

| HARDCOPY UNIT | DI3000 ▸ | NUMBER OF COPIES | 5 ▸ |
|---|---|---|---|
| PROCESSING STATION | VIEWER1 ▸ | FILM FORMAT | 14INX17IN ▸ |
| ARCHIVE STATION | ARCHIEF 12/2 ▸ | | |
| SEND STATION | REVIEWER 8/0 ▸ | | |

| F1 WRITE | F2 CLEAR | F3 RECALL | F4 | | NEW PATIENT F7 | HISTORY F10 | CANCEL |
|---|---|---|---|---|---|---|---|

READY FOR IDENTIFICATION     [HOLD]     26.09.1997     12.46.57

*FIG. 3*

COMBINED IDENTIFICATION AND PREVIEW SYSTEM FOR USE IN DIGITAL RADIOGRAPHY

This application claims benefit of Provisional No. 60/071,641 filed Jan. 16, 1998.

DESCRIPTION

1. Field of the Invention

The invention relates to identification and preview of radiographic images that are stored in a photostimulable phosphor screen.

2. Background of the Invention

In the field of digital radiography a wide variety of image acquisition techniques have been developed that render a digital representation of a radiation image.

In one of these techniques a radiation image, for example an X-ray image of an object, is stored in a screen comprising a photostimulable phosphor such as one of the phosphors described in EP-A-503 702.

In a read out station the stored radiation image is read by scanning the screen with stimulating radiation such as laser light of the appropriate wavelength, detecting the light emitted upon stimulation and converting the emitted light into a digital signal representation that can be subjected to different kinds of image processing techniques.

The original or enhanced image can then be transmitted to a hard copy recorder for reproduction of the image on the film size and lay-out of the radiologist's choice and/or it can be applied to a monitor for display.

It can also be processed and evaluated in an off-line review station and/or archived in an archive station.

After read-out the residual image left on the photostimulable phosphor screen is erased so that the screen is again available for exposure.

As in conventional radiography the radiographic image needs identification, i.e. it needs to be associated with a patient. Further, adjustment parameters for the components of the read out device as well as parameters to be used during image processing are to be defined and associated with the radiographic image.

The currently used identification system operates as follows.

A photostimulable phosphor screen is conveyed in a cassette that is provided with an EEPROM having a number of electrical contacts for power supply and read-write transfer of identification data.

The radiologist or operator performs a radiographic exposure of a phosphor screen in the cassette and feeds the exposed cassette into an identification station so that mechanical contact is made between the electrical contact points of the EEPROM on the cassette and contact pins in the identification station.

Then, the identification data of the patient are entered via keyboard into an identification program running on the identification station.

Alternatively, in case the identification station is connected to a hospital information system (HIS) or a radiology information system (RIS), the identification data can be retrieved from the RIS/HIS and entered automatically.

They can be retrieved via a file of known format transmitted over a computer link as has been described in EP-A-674 187.

Further, an examination type identifier is entered. This is performed by selecting a specific examination type (and subtype) out of a hierarchically popped up menu that is displayed on the screen of the identification station.

With an examination type identifier several settings for the read out apparatus, parameters to be used during image processing and parameters that relate to image reproduction etc. are linked. The set of settings and parameters was stored in advance in each of the stations where it is to be used according to a customisation procedure as has been described in EP-A-679 909.

Then, the patient identification data and the examination type identifier are written into the EEPROM on the exposed cassette.

Further details on this procedure as well as on the outlook of the cassette are described in U.S. Pat. No. 4,960,994.

The exposed and identified cassette is then fed into a read out station where the data stored in the EEPROM are read.

Next the radiographic image stored in the photostimulable phosphor screen is read taking into account the settings for the read out apparatus that correspond with the identifier read from the EEPROM.

The read out image is further subjected to processing taking into account the processing parameters corresponding with the identified examination type.

Next, the screen is erased and at least some of the data stored in the EEPROM are erased (or updated).

In an alternative embodiment such as the embodiment described in EP-A-727 696 the identification data are transferred from a dedicated identification terminal to a radiofrequency tag.

It is common practice to display a preview of the image that is read out from an exposed photostimulable phosphor screen before it is sent to a soft copy or hard copy station or to an archive station etc. The preview image is a low resolution version of the read out and processed image.

The preview gives the operator early feedback on the image quality and allows him to perform a further or a new exposure of the patient in case the image acquisition went wrong or in case the image does not correspond to his expectations.

Several aspects concerning a preview station have been described in EP-A-567 176.

The monitors that are used nowadays as preview monitor are VGA monitors connected via a coaxial cable with a read out apparatus. This implies that the distance between the apparatus where the digital image representation is generated (in case the read out apparatus), is limited and that also the number of monitors that can be connected to the read out system, is limited.

For this reason, a single central preview monitor is commonly used. This monitor is installed in the neighborhood of the read-out apparatus, which apparatus is normally placed outside the radiography rooms. The central preview monitor is then used for display of radiographic images taken in different radiography rooms but read out by the same read out apparatus.

This implies that in most cases an operator who wants to consult the preview monitor has to leave the radiography room and approach the preview monitor in order to wait for the image of his interest to be displayed so that he can evaluate it.

He thus has to leave his patient alone waiting in the radiography room until he has evaluated the image and has decided whether or not further images or retakes are required.

This is not a user-friendly solution.

OBJECTS OF THE INVENTION

It is an object of the present invention to provide a user-friendly preview system for use in the field of digital radiography using photostimulable phosphor screens as intermediary storage medium.

Further objects of this invention will become apparent from the description hereafter.

SUMMARY OF THE INVENTION

The above-mentioned objects are realised by a system for displaying a visual image of a radiation image that has been stored in a photostimulable phosphor screen comprising:
a personal computer having

- means for entering data identifying said radiographic image and for displaying said data,
- means for transferring said data onto an identifying means provided on a cassette conveying said photostimulable phosphor screen,
- means for receiving a digital image representation of said radiographic image read from said screen and for displaying a visual image corresponding with said digital image representation.

The system of the present invention overcomes the disadvantages of the prior art.

A personal computer can be connected to the read out apparatus through an Ethernet connection so that the limitations which were implied by the use of a VGA monitor and coaxial cableconnection no longer exist.

In the system of the present invention the identification function and the preview function are combined on a single personal which is a more user-friendly embodiment.

In one embodiment the means for displaying a visual image are arranged for displaying a mosaic image composed of a number of successively read out images.

In this embodiment reduced image signals representing reduced images comprising less pixels than the original radiation image, are deduced from the digital image representation of the radiation image and a composed signal representing a mosaic type image is formed by means of a number of the reduced image signals.

The composed signal is then applied to a monitor.

In one embodiment, as a new reduced signal is deduced, the composed signal is amended by means of the new signal so that at least one of the reduced images in the displayed image is replaced by the image represented by said new reduced signal.

Preferably a first in, first out order is applied.

The reduced signal can be obtained by sub-sampling or interpolation.

Alternatively in case image processing is applied that is based on decomposition of an image into a multi-resolution representation, amendment of the multi-resolution representation and reconstruction as will be described in greater detail further on, the reduced image can be obtained as a low resolution approximation.

Still alternatively it can be an intermediate image obtained during reconstruction up to some intermediate resolution level.

Preferably a processed image of 1024 times 1024 pixels is calculated in the processing unit of the read-out station or in a separate processing station. This low resolution image is sent to the preview station where it is stored. The number of pixels in the image that is sent to the preview station is preferably 1024×1024 because this number corresponds with the resolution of currently available display screens. However, this number can be configurated.

In the preview station a mosaic type image is composed. Different lay outs are available (as will be described further on). Composition of most of these lay-outs may require further resolution reduction which is then performed in the identification and preview station.

In a preferred implementation, the means for displaying identification data and the means for displaying a visual image are arranged to simultaneously display a screen comprising identification data and a screen comprising the visual image so that these screens partially cover one another.

In this way it is possible to perform identification of a patient without losing sight of the display of images that are provided by the readout apparatus.

In a specific embodiment the cassette conveying the photostimulable phosphor screen is provided with a radiofrequency tag. Radiofrequency tags are known in the art. These devices operate on the basis of data transfer by means of radiofrequencies emitted by an antenna connected e.g. to a personal computer. A Read/Write coil generates by magnetic induction a constant field strength that is sufficient to power the tag's circuitry and the memory of the tag and to generate a system clock on the tag.

The means for transferring data onto an identifying means provided on a cassette conveying said photostimulable phosphor screen, are then adapted for transferring data through radiofrequency transmission.

BRIEF DESCRIPTION OF THE INVENTION

Figure 2:
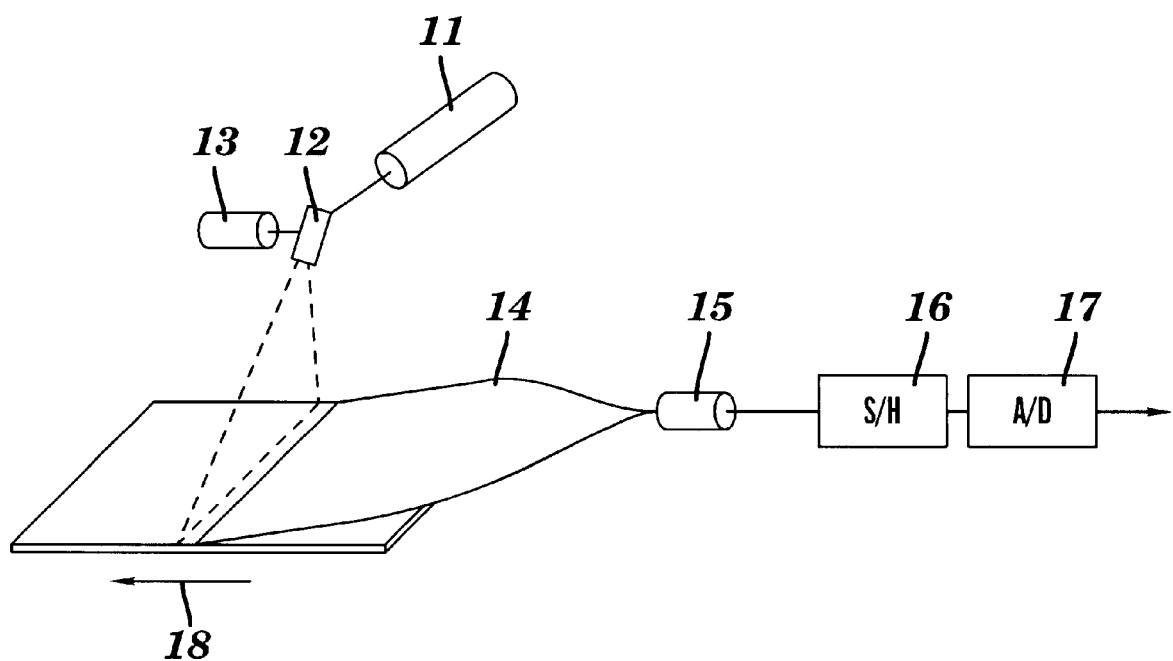
Figure 4:
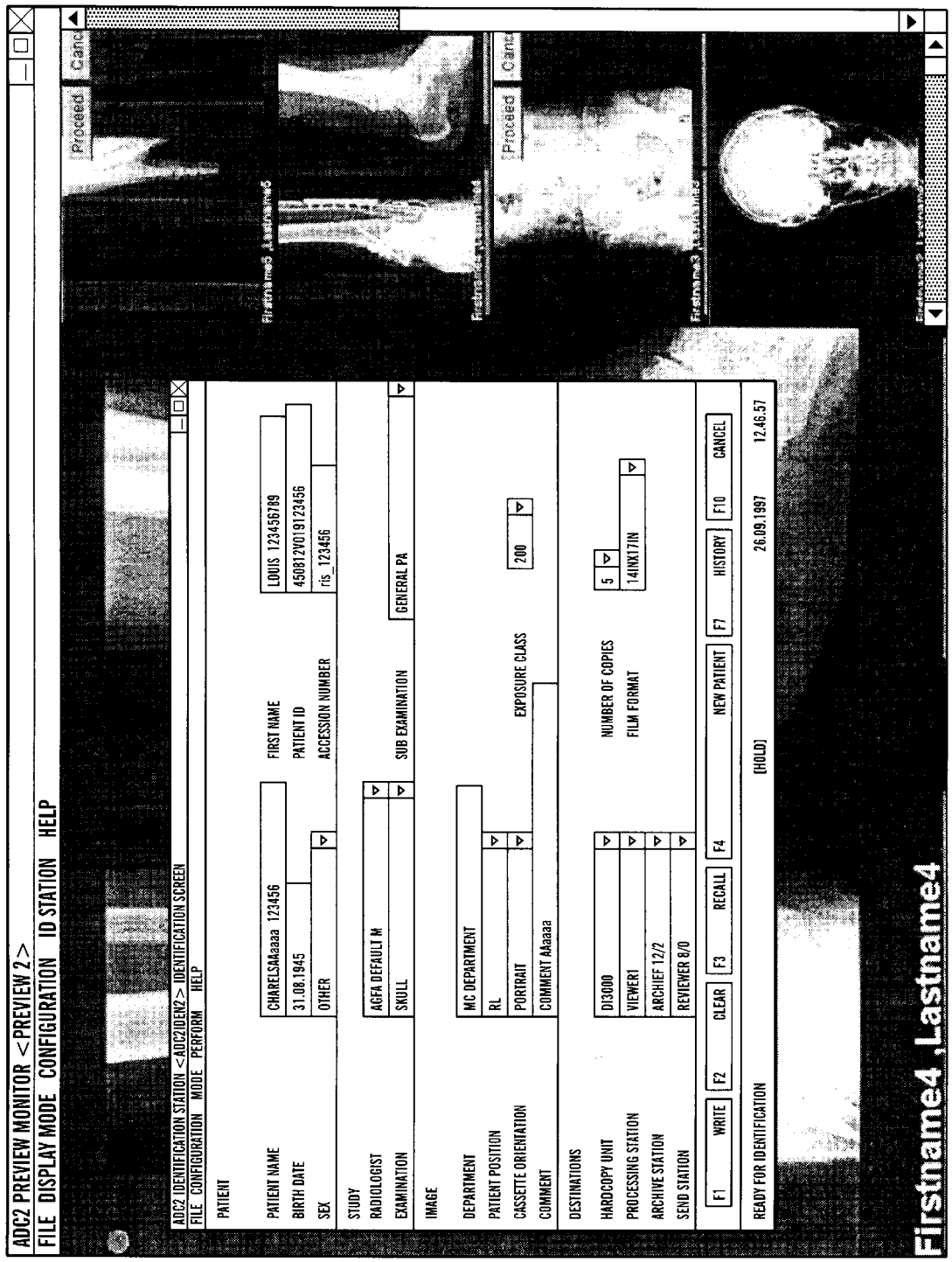
Figure 5:

Further advantages and embodiments of the present invention will become apparent from the following detailed description illustrated by means of the following drawings wherein FIG. 1 schematically shows a digital radiography system, FIG. 2 shows a read-out apparatus for reading an image that has been stored in a photostimulable phosphor screen, FIG. 3 shows an identification screen, FIG. 4 shows an identification screen superimposed on a preview screen, FIG. 5 shows a preview screen.

DETAILED DESCRIPTION OF THE INVENTION

While the present invention will hereinafter be described in connection with preferred embodiments thereof, it will be understood that it is not intended to limit the invention to those embodiments.

The described system is a digital radiography system wherein a radiographic image is recorded on a photostimulable phosphor screen.

The photostimulable phosphor screen is conveyed in a cassette 7. The cassette is provided with a radio-frequency tag 7a in which identification data, i.e. data concerning a patient that is subjected to a radiographic examination and concerning the type of examination that is performed etc., are to be stored.

The system comprises a combined identification/preview station 1, a read-out station 2, a processing station 6 and a laser recorder 3 being interconnected through a network. In read-out station 2 the image stored in the photostimulable phosphor screen is read out and digitised and the digital signal representation of the radiographic image is subjected to image processing in processing station 6. The read out and processed image is then sent to laser recorder 3 to be reproduced. A connection to a hospital information system 9 is also provided.

The system shown in FIG. 1 can be expanded to include other stations such as further workstations for performing off-line processing on the digital representation of the radiographic image and/or for performing soft copy diagnosis, an archive station etc.

The combined identification/preview station 1 consists of a personal computer in a networked configuration. The personal computer has access to hospital information system (HIS) or a radiology information system (RIS) 9.

The identification station is provided with a read/write subunit 4 and an antenna 5 and corresponding steering electronics (not shown) for transferring data to an RF tag.

Although the antenna and the read/write subunit are shown outside the personal computer, it will be clear to the man skilled in the art that other designs are possible. In one embodiment the read/write sub-unit and the antenna are built inside the housing of the personal computer and a slot is provided in said housing into which a cassette can be slided so that the RF tag on the cassette is optimally positioned relative to the antenna.

The identification station is a personal computer loaded with identification and preview software running under Windows 95 or Windows NT or a workstation running under UNIX. The identification and preview software has been written in JAVA language.

This software is an implementation of two different applications, namely the identification application and the preview application which can be activated either separately as stand alone program or combined.

The function of the identification software is to provide identification of a radiographic image stored in an exposed photostimulable phosphor screen. The function of the preview software is to display an image which is read out of a screen and has been subjected to image processing in order to provide early feed back to an operator or a radiologist in case the exposure of the patient went wrong.

The read-out station is illustrated in FIG. 2 and comprises a laser 11 emitting light of a wavelength adapted to the stimulation spectrum of the phosphor used, galvanometric light deflection means 12, 13 for deflecting light emitted by the laser onto the photostimulable phosphor screen, a light guide 14 directing light emitted by a stimulable phosphor screen into the light input face of a photomultiplier 15, a sample and hold circuit 16, and an analog to digital converter 17.

The read-out station is further provided with a means for reading the data stored in the RF tag (not shown). These means comprise an antenna and steering electronics.

The physical location of the RF tag on the cassette is preferably such that its distance from the front edge of the cassette parallel to the fast scan direction and its distance to the centre line parallel to the slow scan direction is fixed for all types of cassettes, so that no mechanical dislocation of the read/write antenna probe in the read-out apparatus is needed with respect to the cassette independent of its physical dimensions.

The read out device also comprises a processing module (not shown) for performing on-line processing on the digital signal representation of the radiation image.

Workflow Description:

The following is a description of the workflow from the identification of a radiation image to the reading of the digital image representation and the transmission of image data and identification data to an output device (such as a hard copy recorder) or to an off-line processing device or an archive station.

A cassette comprising a photostimulable phosphor screen that has been exposed to an X-ray image of a patient is entered into a dedicated slot in an identification station so that a radiofrequency tag provided on the cassette is optimally positioned relative to the antenna in the station.

The identification station runs the identification software so that the graphical user interface (GUI) of the identification software is displayed.

Identification data are entered manually (via keyboard) into the identification station. Alternatively they can be entered through bar code reading or magnetic card reading etc. or they can retrieved from a hospital information system.

FIG. 3 shows the standard identification screen. Several patient identification data are to be filled in such as: patient's name, first name, date of birth, sex, patient identification number, accession number etc.

In the patient name field, the first name field, patient code field, sex field, and date of birth field data are entered by typing. Alternatively they can be retrieved from a hospital (or radiology) information system if this is available The system is also equipped with a patient list and a history list from which data can be retrieved.

The patient list comprises identification data of patients for whom an exposure is planned.

The history list comprises a list of patient and examination data regarding examinations that have already been performed.

Other data such as radiologist related data can be retrieved from a list stored in the identification station at the time of system configuration.

Also data concerning the examination are to be entered: e.g. name of radiologist, examination type etc. The examination field is composed of two fields: examination and sub-examination.

Further, several image identifying data are foreseen among which are an identification of the department, view position, cassette orientation (portrait, landscape), exposure class, comment etc.

For some values such as exposure class, default values are automatically inserted in the screen, once an examination type and examination sub-type is selected. These data are retrieved from a configuration file stored when configuring the system. The comment field allows the user to fill in information depending on his specific needs.

The screen allows also the entering of data concerning the routing of an image, i.e. data concerning the destination to which an image is to be sent following read out. The destinations that are illustrated in FIG. 3 are a hard copy unit, processing station, archive station and send destination (also called soft-copy destination, this is a workstation where the image can be processed and/or displayed).

In the auto-routing mode the destination field (hard copy destination, processing destination, archive and send destination) is automatically filled with the default destination corresponding with the identified examination type and examination subtype, which is obtained from the configuration file loaded at system configuration. However, this field can be changed manually.

A re-routing function gives the user the opportunity to replace a selected destination (for example the destination that corresponds with the examination type and examination sub-type) temporarily by another.

This function can for example be used in case a selected routing is temporarily (one day, on week . . . ) out of use for example due to maintenance. All images that would normally be sent to this destination are then sent to the other destination so that they do not remain in the waiting queue of the device that is out of use.

On the identification screen the operator can select a reproducing apparatus an image is to be sent to. Further, it is common practice to link the reproducing format to the examination type and examination subtype that is selected during the identification procedure. The reproducing format was commonly determined in advance and stored in a configuration file which was loaded into the system at system configuration.

So, it is impossible that an image is sent to a reproducing apparatus which does not support the selected reproducing format. The image is then either not reproduced, or has to be sent to another printer or the format has to be changed.

To solve this problem, the identification station is programmed so that selection of a certain reproducing apparatus limits the choice of available reproducing formats.

A list of available film formats can be configured in advance or updated on-line.

The different fields of the identification screen are filled in by the operator (or filled in by RIS connection). Next, upon termination of this procedure, the identification data are transferred through radiofrequency transmission onto the radiofrequency tag provided on the cassette that was applied into the slot of the identification station.

The identified cassette is then fed into the read out device. As the cassette passes the antenna probe, the information in the RF tag is read out.

Next, the screen is taken out of the cassette and transported in the direction of arrow 18. The operation of the read out station is as follows.

Stimulating rays emitted by laser 11 are directed onto the photostimulable phosphor screen to scan this screen.

The stimulating rays are deflected into the main scanning direction by means of galvanometric deflection means 12, 13. Subscanning is performed by transporting the phosphor screen in the sub-scanning direction indicated by arrow 18.

Upon stimulation, the photostimulable phosphor emits light within a second wavelength range which is different from the wavelength range of the stimulation light. The emitted light is directed by means of a light collector 11 onto a photomultiplier 12 for conversion into an electrical image representation.

Next, the signal is sampled by a sample and hold circuit 16, and converted into a digital raw image signal by means of an analog to digital converter 17. The digital signal representation of the radiation image is then fed into processing module (not shown) where it is subjected to image enhancing signal processing techniques.

A read out image is enhanced by subjecting it to the following image processing.

The image is decomposed into a sequence of detail images at multiple resolution levels and a residual image. Next pixel values of the detail images are modified according to at least one non-linear increasing odd conversion function with a slope that gradually decreases with increasing argument values.

A processed image is then computed by applying a reconstruction algorithm to the residual image and to the set of modified detail images, the reconstruction algorithm being such that if it were applied to the residual image and the unmodified detail images the original image or a close approximation thereof would be obtained.

The conversion function can be defined as $$F(x) = -m^*(-x/m)^p \text{ if } x<0 \text{ and}$$

$$F(x) = x^*(x/m)^p \text{ if } x>0$$

where the power p is chosen within the interval $0<p<1$ and m specifies the abscissa range $-m \leq x \leq m$.

The processing parameters used in the course of the image processing are parameters which corresponds with an examination type identifier read from the RF tag.

A low resolution version of the read out and enhanced image is then sent to identification and preview station 1 where it is stored, sub-sampled if required, used for composition of a mosaic type image and displayed.

Personal computer 1 is programmed so that the preview screen and identification screen are displayed on top of each other whereby the operator can select to keep the identification screen always in top position.

In the described embodiment the computer was programmed so that upon bringing a radiofrequency tag under the antenna that was connected to the personal computer, the identification screen was automatically popped up so as to be filled in by the operator. Upon termination of the identification procedure, the preview screen was shown in front position, thereby covering (at least partially the identification screen).

In order to protect the identification data from inspection by unauthorised people and also to protect the phosphor screen of the personal computer from burn-in, a screen blank was shown after a pre-defined and configurable time out. This screen blank can optionally be protected by means of a password.

It would also be possible to protect the system by making authorisation to use the identification and/or preview station depend on the identification of the operator. Identification of an operator can for example be achieved by reading his identification data from a dedicated identification means such as a radio frequency tag wherein the operator's identification data have been stored.

Different embodiments of the lay out of the preview screen can be selected.

The screen can be composed of a mosaic of for example 6 images pertaining to successively read out images, whereby a first read out image is no longer visualised when a new image is read out and displayed.

An alternative embodiment the preview screen shows a number of small visual images pertaining to successively read out radiation images. The visual images are arranged so that they remain visible when the identification screen is displayed on top of the preview screen or scrolled back to previous images.

Still alternatively a number of small visual images are arranged one above the other in a vertical row shown on the side of the screen whereas the remainder of the screen is filled with a single, larger visual image. The larger image is for example the image which is last read out.

The system is arranged so that the resolution of a displayed images can be changed by the operator. In this way an image of great interest to an operator can for example be shown in an enlarged version when that image is selected by clicking.

On the preview screen a slider is also shown which gives an indication on the exposure characteristics. The slider indicates whether an image has been over- or underexposed.

In this way the operator is immediately warned in case the exposure went wrong so that he can make a new exposure.

Dose monitoring has been described extensively in European patent application EP-A-639 819.

The preview screen is also arranged to optionally display pixels in the image that are saturated either during the process of reading the image out of the phosphor screen or due to window levelling applied to the read out image (as has been described in EP-A-654 761), in different colours.

A read out and processed image is also sent to an output device depending on the destinations entered when identifying the image.

The personal computer is also programmed to be able to perform a so-called hold function. When this function is activated, by activating a corresponding hold key on the identification screen, the image will not be sent to the reproducing station until either a pre-defined period of time has elapsed or until an unhold key provided on the preview screen is activated or the hold key is de-activated.

The hold function provides that the operator can evaluate an image before ordering hard copy recording (or display). In this way reproduction of images that do not correspond with the operator's expectations is prohibited.

What is claimed is:

1. A system for displaying a visual image representation of a radiographic image that has been stored in a photostimulable phosphor screen comprising a personal computer, said computer including:

means for entering data identifying a radiographic image;

means for transferring said identifying data onto an identifying means provided on a cassette conveying said photostimulable phosphor screen;

means for receiving a digital image representation of said radiographic image read from said phosphor screen; and means for simultaneously displaying a screen comprising said identifying data and a screen comprising a visual image corresponding to said digital image representation on a single display, with one of said screens partially covering the other of said screens.

2. A system according to claim 1 wherein said identifying means is a radiofrequency tag and wherein said means for transferring data are adapted to transfer data through radiofrequency transmission.

3. A system according to claim 1 wherein said means for displaying a visual image are arranged for displaying a mosaic image composed of a number of successively read out images.

4. A system according to claim 1 wherein said digital representation has been subjected to image enhancing processing.

5. A system according to claim 1 wherein said means for displaying a visual image are arranged for displaying an indicator of image over-exposure or under-exposure.

6. A system according to claim 1 wherein said means for entering data identifying a radiographic image and for displaying said data comprise means for selecting a destination to which an image is to be sent.

7. A system for displaying a visual image representation of a radiographic image that has been stored in a photostimulable phosphor screen comprising a personal computer, said computer including:

means for entering data identifying a radiographic image and for displaying said data, including means for selecting a destination to which said image is to be sent;

means for transferring said identifying data onto an identifying means provided on a cassette conveying said photostimulable phosphor screen;

means for receiving a digital image representation of said radiographic image read from said phosphor screen and for displaying a digital image corresponding to said digital image representation;

and a hold key, whereby upon activation of said hold key, sending of a read out image to said selected destination is upheld.

8. A system according to claim 7 wherein said hold key is arranged so that sending is upheld for a pre-defined period of time at the end of which the read out image is sent to an identified destination.

9. A system according to claim 7 being arranged so that sending is upheld until de-activation of said hold key.

10. A system according to claim 7 wherein said means for entering data identifying a radiographic image and for displaying said data comprise means for re-routing said destination.

11. A system according to claim 7 wherein said destination is a reproducing apparatus and wherein means are provided for limiting selectable reproducing formats to the formats supported by said reproducing apparatus.

12. A system for displaying a visual image representation of a radiographic image that has been stored in a photostimulable phosphor screen comprising a personal computer, said computer including:

means for entering data identifying a radiographic image, and for displaying said data;

means for transferring said identifying data onto an identifying means provided on a cassette conveying said photostimulable phosphor screen; and means for receiving a digital image representation of said radiographic image read from said screen and for displaying a visual image corresponding to said digital image representation, said means for displaying said image being arranged to display saturated pixels in a color that is different from the color in which said read out image is displayed.

* * * * *